United States Patent
Do

(10) Patent No.: US 11,721,035 B2
(45) Date of Patent: Aug. 8, 2023

(54) SYSTEM AND METHOD OF USE OF AUGMENTED REALITY IN MEASURING BODY CIRCUMFERENCE FOR THE USE OF APPAREL PRODUCTION

(71) Applicant: TAILORU LLC, Massapequa, NY (US)

(72) Inventor: Thu Minh Do, Massapequa, NY (US)

(73) Assignee: TAILORU LLC, Massapequa, NY (US)

( * ) Notice: Subject to any disclaimer, the term of this patent is extended or adjusted under 35 U.S.C. 154(b) by 0 days.

(21) Appl. No.: 17/339,953

(22) Filed: Jun. 5, 2021

(65) Prior Publication Data

US 2021/0390727 A1 Dec. 16, 2021

Related U.S. Application Data

(60) Provisional application No. 63/039,660, filed on Jun. 16, 2020.

(51) Int. Cl.
*G06T 7/60* (2017.01)
*G06T 19/00* (2011.01)
(Continued)

(52) U.S. Cl.
CPC .............. *G06T 7/60* (2013.01); *G06F 3/0488* (2013.01); *G06F 3/14* (2013.01); *G06Q 30/0282* (2013.01); *G06T 7/55* (2017.01); *G06T 19/006* (2013.01); *G16H 40/67* (2018.01); *G16H 50/30* (2018.01); *A61B 5/1079* (2013.01); *G06F 17/17* (2013.01); *G06Q 30/0643* (2013.01); *G06T 2200/24* (2013.01)

(58) Field of Classification Search
CPC ........... G06T 7/60; G06T 7/55; G06T 19/006; G06T 2200/24; G06F 3/0488; G06F 3/14; G06F 17/17; G06Q 30/0282; G06Q 30/0643; G16H 40/67; G16H 50/30; A61B 5/1079

See application file for complete search history.

(56) References Cited

U.S. PATENT DOCUMENTS

| | | | |
|---|---|---|---|
| 6,665,577 B2 | 12/2003 | Onyshkevych et al. | |
| 7,905,028 B2 | 3/2011 | Sieber | |

(Continued)

*Primary Examiner* — Chong Wu
(74) *Attorney, Agent, or Firm* — Myers Wolin, LLC

(57) ABSTRACT

The present invention discloses a system and method for improvement in process of measurement of body circumference using Augmented Reality (AR) and 4-point mathematical calculations approach and mobile device camera. The method includes the steps of receiving two or more individual parameters from an individual device; receiving at least one set of 4 points capture through AR technology; measurement through AR technology from the individual device, at least one dimension including user's inputs on height, weight, age, and size range; performing body segmentation on at least one dimensions to identify one or more body features associated with the human from the background; performing the distance calculation between four points; compare the calculation results with standard sizing database and displaying the final output to the individual. The application utilizes Augmented Reality for estimating the circumference body measurements of an individual from specific point to point capture in the individual's environment using the individual's device.

20 Claims, 9 Drawing Sheets

(51) Int. Cl.

| | |
|---|---|
| *G06F 3/0488* | (2022.01) |
| *G06T 7/55* | (2017.01) |
| *G06F 3/14* | (2006.01) |
| *G16H 40/67* | (2018.01) |
| *G06Q 30/0282* | (2023.01) |
| *G16H 50/30* | (2018.01) |
| *A61B 5/107* | (2006.01) |
| *G06F 17/17* | (2006.01) |
| *G06Q 30/0601* | (2023.01) |

(56) References Cited

U.S. PATENT DOCUMENTS

| | | | |
|---|---|---|---|
| 8,806,765 B2 | 8/2014 | Tulin | |
| 9,737,239 B2 | 8/2017 | Kimmel | |
| 9,799,064 B2 | 10/2017 | Ohnemus et al. | |
| 9,996,981 B1* | 6/2018 | Tran | G06K 9/4671 |
| 10,393,490 B2 | 8/2019 | Park et al. | |
| 10,657,709 B2 | 5/2020 | Moore et al. | |
| 10,706,262 B2 | 7/2020 | Makeev et al. | |
| 2014/0160264 A1* | 6/2014 | Taylor | G02B 21/008 |
| | | | 348/79 |
| 2014/0165265 A1 | 6/2014 | Tulin et al. | |
| 2014/0285522 A1* | 9/2014 | Kim | G06Q 30/0601 |
| | | | 345/633 |
| 2015/0302505 A1* | 10/2015 | Di | G06K 9/00362 |
| | | | 705/26.7 |
| 2016/0247017 A1* | 8/2016 | Sareen | G06T 7/60 |
| 2016/0379408 A1* | 12/2016 | Wright | G06F 3/013 |
| | | | 345/633 |
| 2017/0032444 A1 | 2/2017 | Cooper et al. | |
| 2017/0064214 A1* | 3/2017 | Zhang | G06T 19/20 |

\* cited by examiner

FIG.5

SYSTEM AND METHOD OF USE OF AUGMENTED REALITY IN MEASURING BODY CIRCUMFERENCE FOR THE USE OF APPAREL PRODUCTION

CROSS-REFERENCE TO RELATED APPLICATIONS

This application claims priority to the following U.S. Provisional Patent Application, of which is hereby incorporated by reference in its entirety: U.S. Application No. 63/039,660 filed on 16 Jun. 2020.

BACKGROUND

Field of the Invention

This invention relates to measurements of the circumference of a person's body, and more particularly related to a system for creating an application in the field of individual-guided body measurement tool and pertain particularly to extracting body measurements of individuals using Augmented Reality and 4-points mathematical equation on a mobile phone.

Description of the Related Art

An important use of measurements is to size individuals for apparel. The term "apparel" may encompass garments of any kind: shirts, shoes, hats, etc.

It is clear that body measurements may be used for many other purposes-such as surgical planning, fitness applications, and biometrics—and although this document will focus on sizing individuals for apparel production.

Manual measurement of a person's body has been conducted for thousands of years. Today, the most common way of measuring a person—for example, for sizing a suit—is with a fabric tape measure (often abbreviated to "tape") by professional tailor, optionally accompanied by a set of pins, markers, and pre-sized measurement garments. The tape is used to gauge the length, width, or circumference of various body portions—for example, the circumference of the neck, or the length of the arm from shoulder to wrist—and the pins, markers, and pre-sized garments are used to mark off the measurements from the fabric tape measure, and so establish the overall shape or volume of the body portion. For example, a pre-sized shirt may be donned by an individual, and then portions of that shirt marked or pinned to conform to the individual's body shape, in this way creating a physical "shell" or physical mockup of the person's approximate shape.

Manual measurement suffers from many drawbacks. It is imprecise. The accuracy of the measurements varies depending on the skill of the measurer, the precise location on the body where the measurements are obtained, the stance of the measured individual, and myriad other factors.

It is perishable. The size of an individual changes over time, due to exercise, growth, diet, or even salt intake (affecting tissue volume), so that measurements become stale or obsolete over time. It is time-consuming. Measurement for a suit, for example, easily encompasses fifty or more of measurements, each of which may take seconds to minutes to accomplish.

It is not self-administered. Because it is infeasible to measure oneself, it is usually necessary for an individual to visit a tailor or garment store to be measured (or at least have a friend do it). The individual typically must travel to the measurement site, wait to be seen, and finally wait to be measured. There is also the inconvenience or potentially being pricked by sharp pins if they are used during the sizing process. Furthermore 'it requires prior how-to knowledge', meaning that the individual don't often know how to measure, for very precise and varying measurements.

It is resistant to correction. If errors are made during the measurement process, resulting, say, an ill-fitting shirt, then the individual must return to the measurer to be re-measured. Furthermore, all the measurements may have to be redone from scratch, because it may not be clear which particular measurement was the cause of the mis-sized garment. It is not private. It may be embarrassing or uncomfortable for a person to submit to being measured by someone else while wearing tight clothes or under garments.

There are multiple approaches that have been tried to generate or extract body measurements from images of individuals. A first approach was to use 3D cameras that provide depth data, such as MICROSOFT KINECT camera. With depth sensing, 3D body models can be built to capture body sizing. However, not everyone has access to 3D cameras, and since there is no clear path to mass adoption at the moment, it is not currently conceivable that such 3D cameras become ubiquitous.

A second approach was to use 2D cameras to capture 2D videos, and make use of 2D-to-3D reconstruction techniques and computer vision to recreate 3D body models to capture body sizing. Such a technique is used by companies such as MTAILOR. In the 2D video approach, a 3D body model is recreated using computer vision, and the approach attempts to perform a point cloud matching technique to match an existing 3D body template with a pre-filled point cloud onto the newly created 3D body. However, the result may not be accurate when trying to fit an existing template onto a unique individual's 3D body. After the matching of the template 3D body with the individual's 3D body is complete, sizing and measurements are obtained, but they are generally not accurate. In this approach, someone else needs to take this video for the individual. It is not self-administered.

A third approach was to use 2D cameras to capture 2D photos instead of 2D videos, and similar to the previous method, utilize 2D-to-3D reconstruction techniques with computer visions to capture body sizing. Such a technique is used by 3DLook, for example, a company that has developed 3D reconstruction and measurements from 2D photos into 3D models. Using 2D photos, instead of 2D videos, may involve photos captured at a higher resolution and highly dependent on background quality, the individual is in a static pose with no movement thus producing results with slightly higher accuracy onto 2nd approach, but the other aforementioned problems remain.

In the existing methods using 2D videos or photos or computer vision, 3D body models are generated, and these approaches generally require the individual to have specific poses, stand at a specific distance from the camera, in front of an empty background, wear tight fitting clothing, and/or be partially nude wearing only underwear. Such requirements for controlled environments and significant individual frictions are undesirable. Furthermore, it should be circumference (i.e., Neck, Chest, Waist, and hips). Also, that they don't take into consideration the individual's garment preference—for example: how long the sleeve should be is a unique preference. It has been observed that 1 in 3 garments are returned because of fit due to lack of individual's preference measurement.

Accordingly, many schemes have been proposed to partially or fully improve the process of body measurement.

There are multiple inventions that have been found in this regard. For instance, U.S. Pat. No. 8,806,765B2 Shaped fit sizing system is issued to Levi Strauss and Co. The patent is on a revolutionary, new sizing and fitting system for jeans is based on the concept of shape, not size. This sizing and fitting system is organized around some basic body shapes categories: e.g., slight curve (straighter figure, flatter fanny), demi curve (evenly proportioned hip and seat) and bold curve (smaller waist, larger seat). To use the system, the consumer finds their shape using a shape measuring tool. The shape measuring tool calculates a shape category based on a differential of two measurements in the seat area. With this shape category information, the consumer can easily locate a pair of form-fitting jeans. The sizing and fitting system is also applicable to pants, shorts, skirts, and other clothing where form fit is desirable in the seat and hip area.

Another patent on Systems and methods for tracking body surfaces of individuals bearing U.S. Pat. No. 9,737,239B2 is issued to ATLAS5D Inc. The patent is on a system for sizing and fitting an individual for apparel, accessories, or prosthetics includes at least one energy emitter configured to emit energy onto a field-of-view that contains an individual, and at least one energy sensor configured to capture reflected energy from within the field-of-view. A spatial measurement module calculates spatial measurements of a surface portion of the body of the individual when the individual is either stationary or moving about in real-time, based on data from the energy sensor.

Another patent on Systems and methods for collecting body measurements, virtually simulating models of actual and target body shapes, ascertaining garment size fitting, and processing garment orders bearing U.S. Pat. No. 7,905,028B2 is issued to Stephen Sieber. The patent is on methods and systems are provided for obtaining coordinated body measurements of an individual using a measuring device having a belt with a first scale of measurement indicia and a strip with a second scale of measurement indicia. Also provided are a method and system of virtually rendering a simulated model of an actual body shape and a target body shape of an individual. Methods and systems of size fitting garments and processing garment orders are also provided.

A Shaped Fit Sizing System with Body Shaping bearing US patent 2,014,0165265A1 is issued to Levi Strauss and Co. The patent is on jeans are fitted based on the concept of shape, not size. There are at least three shape categories for different levels of curviness. With shape category information, the consumer can more easily find and fit a pair of form-fitting jeans. These jeans can also include a body shaping panel on an inside surface of a material of the pants to help actively shape the body. The body shaping panel enhances the body's natural curves while de-emphasizing the body's flaws, so the consumer can feel confident and attractive in their jeans.

Another patent on Self-measuring garment bearing US patent 2,017,0032444A1 is issued to Like A Glove Ltd. The patent is on measurement apparatus includes an elastic fabric, configured as a garment (20, 80) to be worn over a part of a body of a subject. One or more conductive fibers (22, 24, 25, 92, 93) are integrated with the elastic fabric to as to stretch together with the elastic fabric when worn over the part of the body. A controller (26) is coupled to measure an electrical property of the one or more conductive fibers in response to stretching of the elastic fabric, and to output an indication of a dimension of the part of the body based on the measured property.

A Garment fitting system and method bearing U.S. Pat. No. 9,799,064B2 is issued to Eyefitu AG. The patent discloses at least one database is accessed that includes at least personal size information representing measurements respectively associated with at least one person. Clothing information is received that represents at least one of the plurality of articles of clothing. The received clothing information is processed to associate the clothing information with at least some of the personal size information associated with one of the plurality of persons. Thereafter, a value is determined, as a function of the processed clothing information, that represents the fit of the one of the articles of clothing with at least one person. Information associated with the information is displayed.

A System, method and article of manufacture for automated fit and size predictions bearing U.S. Pat. No. 6,665,577B2 is issued to True Fit Corp. The patent relates to an automated system, method and article of manufacture for determining the most appropriate fit and size of a garment, based on either or both customer preference or/and set objective criteria, for a particular garment dimension or a plurality of garment dimensions as they relate to a consumer body dimension or dimensions and the ideal body dimension or dimensions for that garment or for a range of garments.

A Length measuring device and length measuring system bearing U.S. Pat. No. 10,393,490B2 is issued to Bagel Labs Co Ltd. The patent is on a length measuring device and a length measuring system are provided, in which the length measuring device includes a casing, a first rotating portion accommodated in the casing, and rotated with a portion of a circumference thereof being exposed out of the casing and in contact with an object to be measured, a first sensing portion which senses an amount of rotation of the first rotating portion, and a controller which converts the amount of rotation of the first rotating portion into length measurement. Additionally, the length measuring device may further include a second rotating portion coiled with a strip by a plurality of times, and rotated according to the strip being withdrawn or retracted through an outlet formed in the casing, and a second sensing portion which senses an amount of rotation of the second rotating portion, in which the controller may convert the amount of rotation of the second rotating portion into length measurement.

A patent U.S. Pat. No. 10,706,262 B2 issued to Fit3D Inc on a method for estimating the body measurements of a subject from at least two photographic images of the subject. The method includes capturing the photographic images using a digital imaging device, for example, a mobile device camera, and estimating the body measurements of the subject using heat map data generated by an intelligent computing System such as a trained neural network. A patent U.S. Pat. No. 10,657,709B2 issued to Fit3D Inc. on Generation of Body Models and Measurements on the method of measurements or models of a human body are generated. An image of the human body may be identified and a fiducial map may be generated. The fiducial map may be compared to pre-processed fiducial maps stored in a data store. A plurality of pre-processed fiducial maps of human bodies may be identified when a correlation between the fiducial map and the pre-processed fiducial maps exceeds a defined threshold. A silhouette image of the human body may be generated based on the image and may be compared to pre-processed silhouette images associated with the plurality of pre-processed fiducial maps. One of the pre-processed silhouette images may be identified when a correlation value between the silhouette image and the pre-processed silhouette images exceeds a defined threshold.

There are multiple solutions that have been presented in prior patent art. However, these solutions are limited and restricted to focus on technology such as 2D 3D mapping and computer vision. The current invention is focused on presenting an assembly which is directed to system and method to estimate human body shape from sensor data to be able to capture the curvature and circumference of the body using the point-to-point AR technology. The current invention focus on the point-to-point Augmented Reality Kit (ARKit) technology which allows the individual to capture 4 measurement points in space for each circumference (for example, Neck, Waist, Hips) in relation to the individual's current environment, which is passed through 2 mathematical equations to calculate the location of the measurement points in space and the distance between the points to form the circumference, which is then matched with the individual's person height, weight, and garment system sizings, which then present the accurate circumference measurement of the individual's body measurement.

To make this possible and intuitive, the invention uses a low-dimensional 3D model of the human body is employed that accurately captures details of the human form by using a mobile phone camera. The method captures the individual's preference because the individual can point the phone to the measurement point that they want for the garment (for example, if someone likes to wear long sleeve, they can adjust the point where they want the sleeve to end.) This is important because other technology only capture exact accurate measurements while our technology allows individual to capture preference. Furthermore:

it is not dependent on background quality;
Use of mobile phone which everyone has;
Self-administrated.

The technology is based on the use of Augmented Reality (ARKit) and 4-points mathematical equation on a mobile phone to measure the body circumference. The individual is guided throughout the process. For example, neck, chest, hip. First it starts by asking the individual of their body height, weight, and clothing sizing ranges. The system then prompts for measurements they would want to measure. The individual is then guided to point the phone face down towards their skin at 4 different points on the measurement (chest for example) front to back, then side to side. The phone capture the 4 points in space with its camera in relation to the environment around these points (Augmented Reality). The algorithms calculate the body measurement circumferences based on the distance between these 4 points to determine using two mathematical equations below:

(1) Edward Furey came up with this one to calculate the distance between two 3D points in space. X, y, z are the coordinates of each point in space:

$$d=\sqrt{(x2-x1)2+(y2-y1)2+(z2-z1)2}$$

(2) to calculate the curvatures based on these two distances we use ellipse perimeter. The famous Indian mathematician Ramanujan came up with this better approximation:

$$\text{approx } pi[3(a+b)-\text{sqrt}((3a+b)(a+3b))].$$

The circumference body measurements are then compared to backend standard sizing data grid to check for accuracy. This is finished by displaying the actual body measurements to the individual on screen and guide them to fix any inaccurate measurements so they can send the right measurements to their tailors or clothing brand to make a perfect fit garment.

None of the previous inventions and patents, taken either singly or in combination, is seen to describe the instant invention as claimed. Hence, the inventor of the present invention proposes to resolve and surmount existent technical difficulties to eliminate the aforementioned shortcomings of prior art.

SUMMARY

In light of the disadvantages of the prior art, the following summary is provided to facilitate an understanding of some of the innovative features unique to the present invention and is not intended to be a full description. A full appreciation of the various aspects of the invention can be gained by taking the entire specification, claims, drawings, and abstract as a whole.

The primary desirable object of the present invention is to provide a novel and improved method of a body measurement system which allows individual to measure their circumference body parts by using augmented reality and 4-points mathematical equations.

Another object of this invention is to provide a new and improved method which utilizes a camera, in order to obtain depth data and the phone captures the 4 points in space with its camera in relation to the environment around these points.

It is an additional object of the invention to provide such an improved system which does not require 3D scanning nor the use of wearable markers; for example, a full 360-degree panoramic view of the individual is not required.

It is another object to provide an improved system which does not require a separate human operator (other than the individual who is being measured).

It is another objective of the invention to provide a low-cost, compact, portable, and affordable system for measurement.

It is also the object of the invention to provide an assembly which enables garment-fitting in an individual's own home.

It is further the objective of the invention to provide a highly automated system and does not require special training or skills to operate.

It is moreover the objective of the invention to provide fast and convenient approach, allowing an individual to easily take measurements whenever and as often as desired, thus addressing the problem of "perishable" measurements that become inaccurate as time passes.

It is further the objective of the invention to offer privacy, because the individual does not need to travel outside of his/her own home and is able to execute the present system and method alone, and because the present system and method neither collects nor transmits detailed 3D models of the individual's body.

It is further the objective of the invention allowing individual to move about while body measurements are being acquired, without having to pose, in contrast to a 3D scanner, where the individual must remain perfectly still while being scanned.

It is also the objective of the invention to provide a smart assembly which provide ease of use and convenience to the individual and provides accurate measurements based on the individual's height, weight, and standard garment sizing system.

Thus, it is the objective to provide a new, cost convenient, and private system and method of sizing virtually any desired surface portion of a person's body. Other aspects, advantages and novel features of the present invention will become apparent from the detailed description of the invention when considered in conjunction with the accompanying drawings.

This Summary is provided merely for purposes of summarizing some example embodiments, so as to provide a basic understanding of some aspects of the subject matter described herein. Accordingly, it will be appreciated that the above-described features are merely examples and should not be construed to narrow the scope or spirit of the subject matter described herein in any way. Other features, aspects, and advantages of the subject matter described herein will become apparent from the following Detailed Description, Figures, and Claims.

BRIEF DESCRIPTION OF DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

Figure 1:
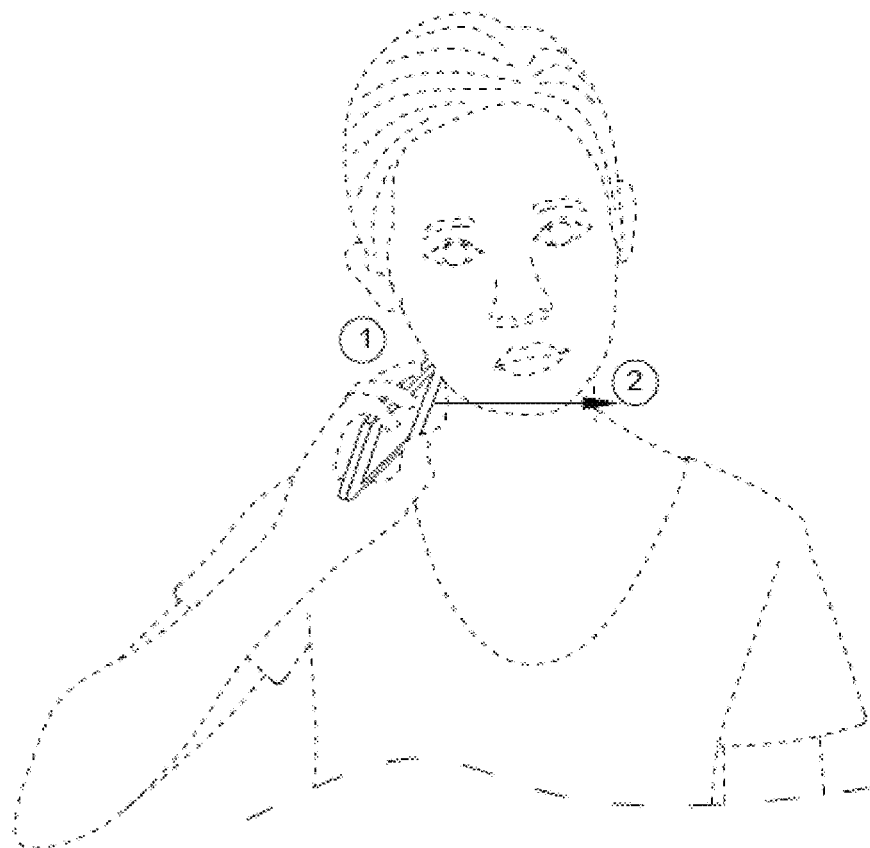
Figure 2:
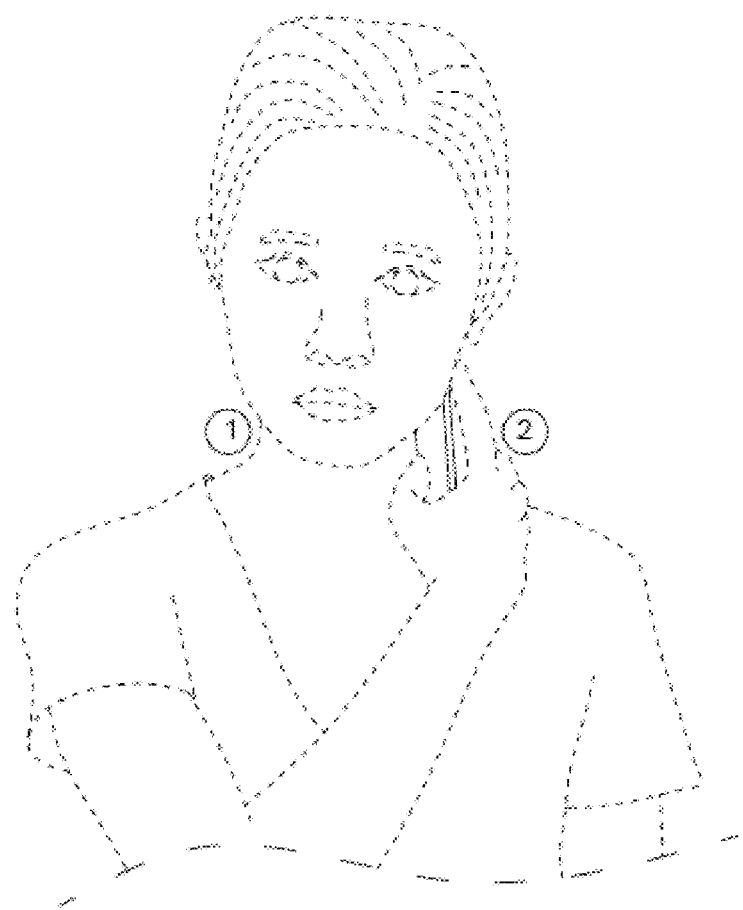
Figure 3:
Figure 4:
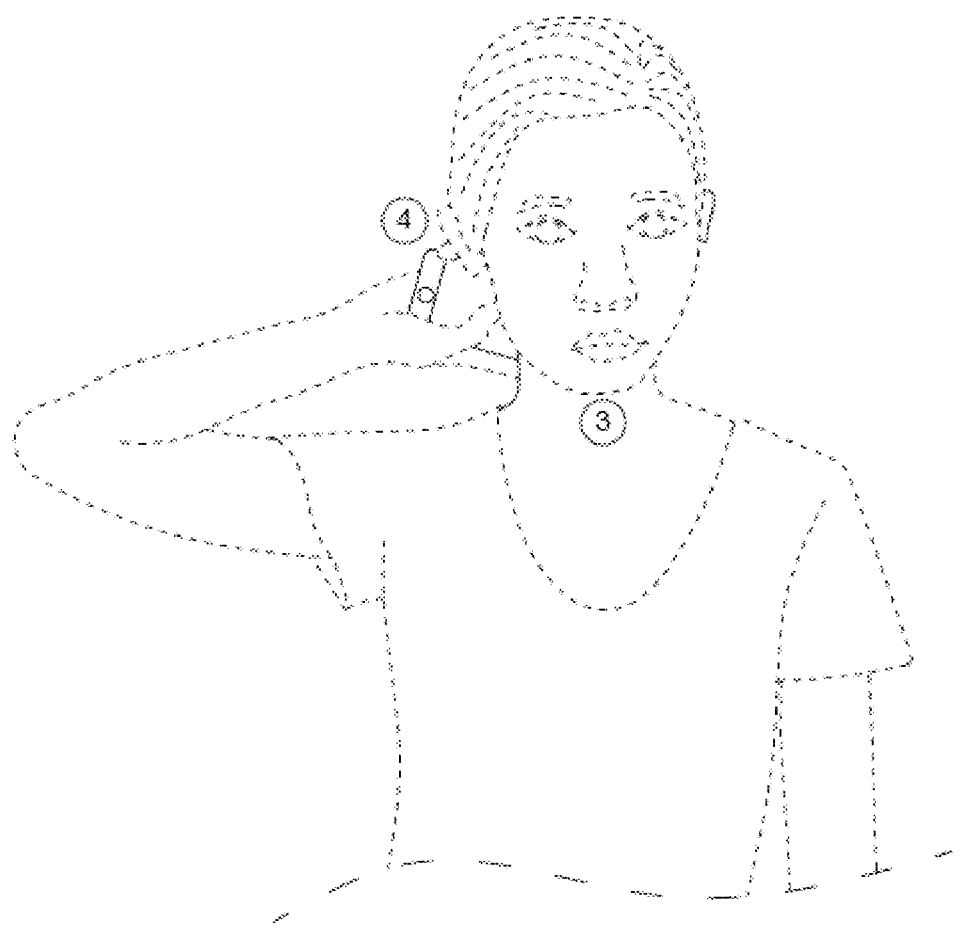
Figure 6:
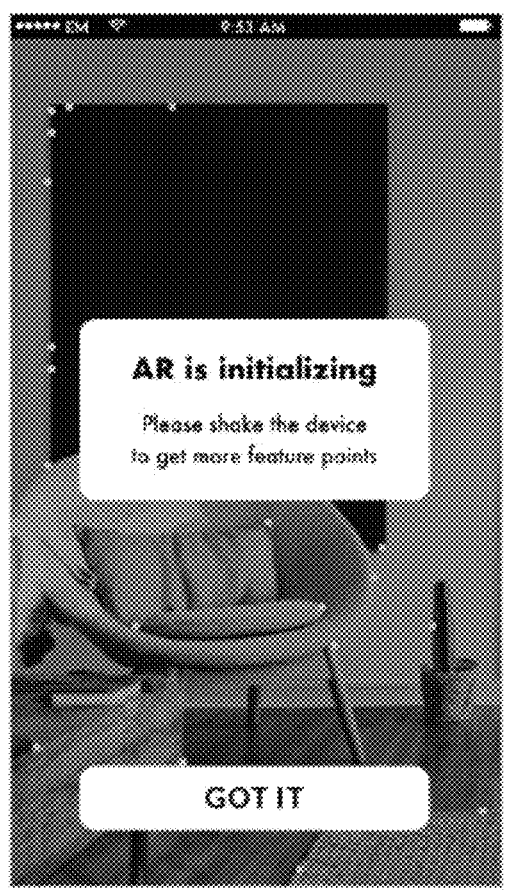
Figure 7:
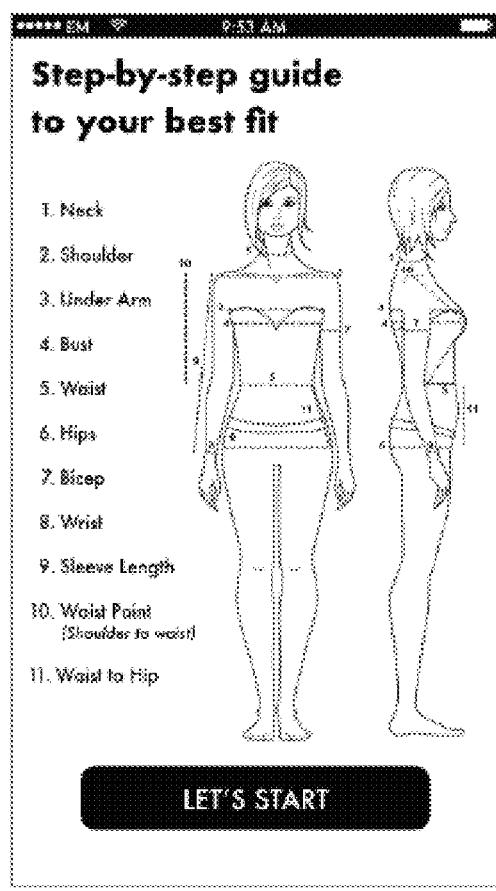
Figure 8:
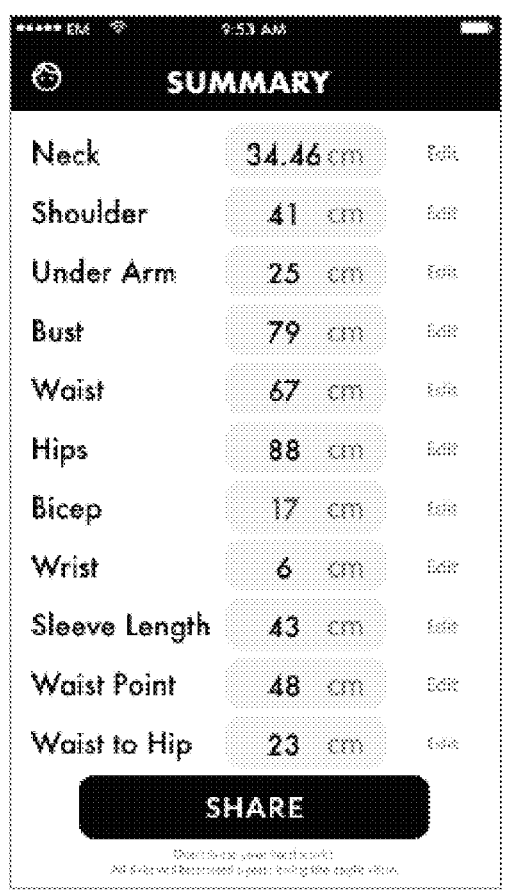
Figure 9:
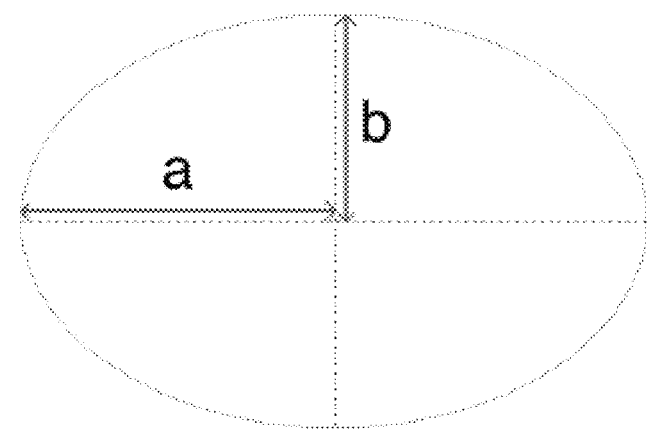

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

a. FIG. 1 to 4 illustrate the method of measurement with an individual taking a neck circumference measurement using the mobile device by pointing to four points around the neck.

b. FIG. 1 shows the individual capturing the right point of the neck using a mobile device.

c. FIG. 2 shows the individual capturing the left point of the neck using a mobile device.

d. FIG. 3 shows the individual capturing the front point of the neck using a mobile device.

e. FIG. 4 shows the individual capturing the back point of the neck using a mobile device.

f. FIG. 5 shows the mobile device screen to capture the individual's height, weight, and standard size system range to be used for checking measurement accuracy.

g. FIG. 6 shows the augmented reality calibration to capture the individual's current environment, then to be able to capture the individual in the current environment.

h. FIG. 7 shows the step-by-step guide for each body feature's measurement.

i. FIG. 8 shows a summary of the captured measurements for apparel production.

j. FIG. 9 illustrates the a and b distance between the 4 points, in reference to mathematical formula by Indian mathematician Ramanujan.

DETAILED DESCRIPTION

Detailed descriptions of the preferred embodiment are provided herein. Specific details disclosed herein are not to be interpreted as limiting, but rather as a basis for the claims and as a representative basis for teaching one skilled in the art to employ the present invention in virtually any appropriately detailed system, structure or manner.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

The present invention is directed to provide an improved system of utilizing augmented reality and mathematical calculations to measure body circumference an individual without any further assistance.

The present-day difficulty of apparel production is easily apprehended. The sizes of clothing items are not consistent across manufacturers or countries, and desired sizes are often out-of-stock at retail stores, or simply non-existent. Consumers must typically travel from store to store seeking clothing that fits "well enough" or go to a tailor to get specifical measured which can be inconvenient and costly. Embodiments of the present system and method prepare standardized types of measurements that are applicable to all types of apparel production and that may be translated across all brands.

Although, as noted above, kiosks utilizing 3D scanners are becoming available in the retail setting, they still impose inconvenient travel on the consumer, who must go to the location of the scanner; may impose wait times on the consumer, who might have to stand in line behind others to use the 3D scanner; and require the consumer to return to the store if any measurements were missed or have to be repeated. Embodiments of the present system and method are designed to be used at home, as much and as often as the individual wishes.

The desire for privacy may assume particular prominence in some special circumstances, such as illness or injury, For example, breast cancer victims who have undergone mastectomies may wish to carry out private measurements to aid in the purchase of specially-shaped bras.

Some embodiments of the discussed system are able to carry out measurements using Augmented Reality for Custom Clothing Measurement with apparel production. Augmented Reality uses the phone front facing camera to map the environment the individual is in using ARKit calibration. It then utilizes a foreground segmentation component within the calibration and data pre-processing system identifying the location of the person in a frame as distinct from the background. Standard techniques for image data use statistical measures of image difference between an image with and without a person present. For a new image with the person present, a statistical test is performed that evaluates how likely the pixel is to have come from the background model. Typically, a probability threshold is set to classify the pixel. After individual pixels have been classified as foreground or background, several image processing operations can be applied to improve the segmentation, including dilation and erosion, median filtering, and removal of small disconnected components. This leads to the accurate location of each body measurement point in the individual's environment. For each measurement, there may be multiple points. For example, a Neck measurement requires the capture of 4 points in space (front/back/left side/right side)

More specifically, in various embodiments, the present invention is a AR method for generating body size measurements of a human, the computer-implemented method executable by a phone hardware processor, the method comprising receiving two or more individual parameters from an individual device; at least two inputs for a straight line measurement (a Sleeve Length) and four inputs for a circumference measurement of a body feature (a Neck); at least two inputs containing the human and a background; AR is performing body measurements based on user-selected body feature by capturing each of the 4 measurement point in space, finding the distance between those points, and through math calculations create the circumference of the selected body feature, generating guided annotation lines on each body feature corresponding to a standard sizing database that have been separately trained on each body feature; generating the final accurate body measurements for the chosen body feature.

In an embodiment, at least one input comprises at least a one right side measurement to a left side measurement of the human, and at least a one front side measurement to a back side measurement and the method further comprises the following steps after the performing annotation step: calculating at least one circumference of at least one annotated body feature utilizing line-annotated front-view and side-view dimensions and a height of the human; and generating the body feature measurements from the at least one circumference utilizing the sizing based on the at least one circumference, the height, weight and standard sizing database and the one or more individual parameters.

In an embodiment, the measurement process comprises of receiving two or more individual inputs of the individual parameters through the individual device.

In an embodiment, the receiving the one or more individual parameters from the individual device comprises receiving individual input of the individual parameters through the individual device.

In an embodiment, the distance between two 3D points in space is calculated by:

$$d=\sqrt{(x2-x1)^2+(y2-y1)^2+(z2-z1)^2}.$$

https://www.calculatorsoup.com/calculators/geometry-solids/distance-two-points.php The Indian mathematician Ramanujan also came up with this formula.

Furey, Edward "3D Distance Calculator"; CalculatorSoup, https://www.calculatorsoup.com. Online Calculators.

In an embodiment, the curvatures based on these two distances is calculated by ellipse perimeter approx. The famous Indian mathematician Ramanujan came up with this better approximation:

$$pi[3(a+b)-\sqrt{((3a+b)(a+3b))}].$$

In an embodiment, the results from the math equations are compared to standard sizing data grid to check for accuracies that correspond to a given measurement of the human's body feature.

In an embodiment, the at least one measurement or complete measurements are displayed to the individual.

While a specific embodiment has been shown and described, many variations are possible. With time, additional features may be employed. The particular shape or configuration of the platform or the interior configuration may be changed to suit the system or equipment with which it is used.

Having described the invention in detail, those skilled in the art will appreciate that modifications may be made to the invention without departing from its spirit. Therefore, it is not intended that the scope of the invention be limited to the specific embodiment illustrated and described. Rather, it is intended that the scope of this invention be determined by the appended claims and their equivalents.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

The invention claimed is:

1. A system for capturing body measurements comprising:
   a handheld device having a sensor module for locating the handheld device in space; and
   a user interface for utilizing Augmented Reality (AR) to capture a user's body measurements, the user interface configured for instructing the user in locating the handheld device relative to the user's body or an environment;
   wherein the handheld device is configured to identify a measurement of the user to be captured, and wherein, upon identification of the measurement to be captured, the system indicates a plurality of locations relative to the user's body to be recorded, and wherein the handheld device is physically moved to each of the plurality of locations adjacent the user's body and pointed towards the user's skin at each of the plurality of locations, and wherein the sensor module records a location in space associated with each of the plurality of locations,
   wherein the system determines a value for the measurement of the user based on relative locations of the recorded locations in space.

2. The system of claim 1, wherein the measurement of the user to be captured is a body circumference, and wherein the plurality of locations is four locations, and wherein the interface instructs the user in physically moving the handheld device from a first side point to a second side point, followed by a movement from a front point to back point.

3. The system of claim 2 wherein the four locations correspond to locations about the user's neck or waist.

4. The system of claim 2 wherein the measurement of the user is one of a plurality of measurements of the user to be captured, and wherein, upon recording the four locations, the handheld device identifies a secondary measurement of the user to be captured and indicates a secondary plurality of locations relative to the user's body to be identified.

5. The system of claim 4 wherein the four locations correspond to locations about the user's neck and the secondary measurement of the user is a length of an arm.

6. The system of claim 1 wherein the handheld device is a smartphone and wherein the sensor module for locating the device in space comprises a camera.

7. The system of claim 6, wherein the user interface instructs the user in taking at least one image of the environment in which the user is operating the system.

8. The system of claim 7, wherein the system utilizes the at least one image of the environment in combination with information received from the camera for locating the device in space and wherein the value for the measurement of the user is not based on a three-dimensional model.

9. The system of claim 7, wherein the at least one image of the environment comprises a plurality of distinct perspective views of the environment.

10. The system of claim 1, wherein the measurement of the user is one of a plurality of measurements of the user to be captured, and wherein upon recording a plurality of locations associated with each of a plurality of measurements, the handheld device outputs a set of measurements for use in garment creation or fitting.

11. The system of claim 1, wherein the value for the measurement of the user is further based on a known height and weight of the user.

12. A method for capturing body measurements, the method comprising:
providing, at a handheld device, a user interface for capturing body measurements of a user;
displaying an image of a human at the user interface, the image indicating at least one body measurement to be captured;
indicating, in the context of the image of the human, a first target location adjacent the user's body for the handheld device;
instructing the user to locate the handheld device at the first target location and pointed towards the user's skin;
recording a location in space associated with the first target location;
instructing the user to locate the handheld device pointed towards the user's skin at a second target location adjacent the user's body for the handheld device;
recording a location in space associated with the second target location;
determining a value for the at least one body measurement to be captured based on relative locations of the first and second target locations.

13. The method of claim 12, further comprising instructing the user to locate the handheld device pointed towards the user's skin at a third target location adjacent the user's body for the handheld device, recording a location in space associated with the third target location, instructing the user to locate the handheld device pointed towards the user's skin at a fourth target location adjacent the user's body for the handheld device, and recording a location in space associated with the fourth target location, wherein the value for the at least one body measurement to be captured is based on relative locations of the first, second, third, and fourth target locations.

14. The method of claim 13, wherein the at least one body measurement to be captured corresponds to a body circumference, and wherein the first target location is a first side of the circumference, the second target location is a second side of the circumference, the third target location is a front of the circumference, and the fourth target location is a back of the circumference.

15. The method of claim 14, wherein the at least one body measurement is a circumference of the user's neck or waist.

16. The method of claim 15, wherein the at least one body measurement is a first of a plurality of body measurements to be captured, and wherein upon determining the value for the at least one body measurement, the method instructs the user to locate the handheld device at additional target locations corresponding to a second measurement of the plurality of body measurements to be captured.

17. The method of claim 16, wherein the first body measurement is a circumference of the user's neck, and the second body measurement is a length of the user's arm.

18. The method of claim 17, wherein the handheld device comprises a camera, and wherein the method further comprises instructing the user to take at least one image of an environment in which the user is located by way of the camera.

19. The method of claim 18, wherein the recording of the location in space associated with each target location is by way of the camera and is based on the at least one image of an environment.

20. The method of claim 12, wherein the at least one body measurement to be captured is one of a plurality of measurements of the user to be captured, and wherein upon recording a plurality of locations associated with each of a plurality of measurements, the handheld device outputs a set of measurements for use in garment creation or fitting.

* * * * *